US012577725B2

(12) United States Patent
Lan et al.

(10) Patent No.: US 12,577,725 B2
(45) Date of Patent: Mar. 17, 2026

(54) ODOR CONTROL COMPOSITION AND METHOD OF USING

(71) Applicant: Microban Products Company, Huntersville, NC (US)

(72) Inventors: Tian Lan, Huntersville, NC (US); Brian Patrick Aylward, Concord, NC (US)

(73) Assignee: Microban Products Company, Huntersville, NC (US)

( * ) Notice: Subject to any disclaimer, the term of this patent is extended or adjusted under 35 U.S.C. 154(b) by 0 days.

(21) Appl. No.: 16/189,102

(22) Filed: Nov. 13, 2018

(65) Prior Publication Data

US 2019/0145045 A1     May 16, 2019

Related U.S. Application Data

(60) Provisional application No. 62/585,749, filed on Nov. 14, 2017.

(51) Int. Cl.
*D06M 11/83*          (2006.01)
*A61L 9/01*           (2006.01)
(Continued)

(52) U.S. Cl.
CPC .............. *D06M 11/83* (2013.01); *A61L 9/01* (2013.01); *D06M 11/38* (2013.01); *D06M 11/42* (2013.01);
(Continued)

(58) Field of Classification Search
CPC ...... D06M 11/83; D06M 10/04; D06M 11/38; D06M 11/42; D06M 11/44; D06M 11/45;
(Continued)

(56) References Cited

U.S. PATENT DOCUMENTS 5,663,224 A      9/1997   Emmons et al.
5,833,970 A     11/1998   Cox
(Continued)

FOREIGN PATENT DOCUMENTS

JP     H05-156510 A      6/1992
JP     2002339239 A     11/2002
(Continued)

OTHER PUBLICATIONS

Morais et al., Antimicrobial Approaches for Textiles: from Research to Market, https://www.ncbi.nlm.nih.gov/pmc/articles/PMC5456784/pdf/materials-09-00498.pdf. Jun. 2016.*
(Continued)

*Primary Examiner* — Hong Yu
(74) *Attorney, Agent, or Firm* — Jason A. Smith; Shumaker, Loop & Kendrick, LLP

(57)                 ABSTRACT

A chemical composition for controlling odor and to a method of using the chemical composition to impart an odor control treatment to an article, more particularly to a textile material or a building or construction material. The chemical composition comprises a metal compound selected from the group consisting of a metal oxide, a metal hydroxide, and a combination thereof and a sulfo polyester. Methods of making and of using are provided.

8 Claims, 4 Drawing Sheets

Synthetic Sweat Odor Intensity Panel Evaluation 25HL

(51) Int. Cl.

| | |
|---|---|
| *D06M 11/38* | (2006.01) |
| *D06M 11/42* | (2006.01) |
| *D06M 11/44* | (2006.01) |
| *D06M 11/45* | (2006.01) |
| *D06M 11/46* | (2006.01) |
| *D06M 11/49* | (2006.01) |
| *D06M 13/00* | (2006.01) |
| *D06M 15/263* | (2006.01) |
| *D06M 15/507* | (2006.01) |

(52) U.S. Cl.
CPC ............ *D06M 11/44* (2013.01); *D06M 11/45* (2013.01); *D06M 11/46* (2013.01); *D06M 11/49* (2013.01); *D06M 13/005* (2013.01); *D06M 15/263* (2013.01); *D06M 15/5075* (2013.01)

(58) Field of Classification Search
CPC .... D06M 11/46; D06M 11/49; D06M 13/005; D06M 15/263; D06M 15/5075; D06M 16/00; A61L 9/01
See application file for complete search history.

(56) References Cited

U.S. PATENT DOCUMENTS

| | | | |
|---|---|---|---|
| 5,976,193 | A | 11/1999 | Thomas et al. |
| 6,060,229 | A * | 5/2000 | Eichorst ................... G03C 5/14 |
| | | | 430/140 |
| 6,096,491 | A * | 8/2000 | Majumdar .......... G03C 1/7614 |
| | | | 430/529 |
| 6,162,890 | A | 12/2000 | George et al. |
| 6,171,685 | B1 * | 1/2001 | George .................. B32B 27/06 |
| | | | 428/221 |
| 6,454,813 | B1 | 9/2002 | Chan |
| 6,495,079 | B1 | 12/2002 | Gallucci et al. |
| 6,607,994 | B2 | 8/2003 | Soane et al. |
| 6,723,428 | B1 | 4/2004 | Foss et al. |
| 6,979,491 | B2 | 12/2005 | Yan et al. |
| 6,989,193 | B2 | 1/2006 | Haile et al. |
| 7,291,570 | B1 | 11/2007 | Green et al. |
| 7,521,410 | B2 | 4/2009 | Collier et al. |
| 7,585,331 | B2 | 9/2009 | Lai et al. |
| 7,597,718 | B2 | 10/2009 | Yoshikawa et al. |
| 7,754,625 | B2 | 7/2010 | Hendriks et al. |
| 7,794,737 | B2 | 9/2010 | Fish et al. |
| 7,862,624 | B2 | 1/2011 | Tran |
| 8,021,584 | B2 | 9/2011 | Studholme et al. |
| 8,277,518 | B1 | 10/2012 | Kramer et al. |
| 8,512,417 | B2 | 8/2013 | Miller et al. |
| 8,690,964 | B2 | 4/2014 | Kramer et al. |
| 9,175,147 | B2 | 11/2015 | Ton-That et al. |
| 9,180,487 | B2 | 11/2015 | Weinelt et al. |
| 9,200,086 | B2 | 12/2015 | Wan et al. |
| 9,234,310 | B2 | 1/2016 | Kramer et al. |
| 9,284,682 | B2 | 3/2016 | Kramer et al. |
| 9,487,912 | B2 | 11/2016 | Swamy et al. |
| 9,986,742 | B2 | 6/2018 | Toreki et al. |
| 10,011,944 | B2 | 7/2018 | Poldervaart |
| 10,065,887 | B2 | 9/2018 | Kierat et al. |
| 2003/0190266 | A1 | 10/2003 | Tsurumi |
| 2004/0142831 | A1 * | 7/2004 | Jager Lezer ............. A61K 8/88 |
| | | | 510/130 |
| 2006/0123560 | A1 | 6/2006 | Johschker et al. |

| | | | |
|---|---|---|---|
| 2006/0127335 | A1 | 6/2006 | Nakamura |
| 2006/0171996 | A1 | 8/2006 | Sakai |
| 2006/0265814 | A1 | 11/2006 | Ritter |
| 2007/0071933 | A1 | 3/2007 | Gavelli et al. |
| 2008/0299154 | A1 * | 12/2008 | Barrios ................... A61K 8/042 |
| | | | 424/70.6 |
| 2009/0098016 | A1 | 4/2009 | Koper et al. |
| 2009/0311293 | A1 * | 12/2009 | Fratini ................. A61K 8/0208 |
| | | | 424/401 |
| 2010/0003296 | A1 | 1/2010 | Cheng et al. |
| 2010/0136075 | A1 | 6/2010 | Militz et al. |
| 2011/0023206 | A1 | 2/2011 | Dunn et al. |
| 2011/0150808 | A1 * | 6/2011 | Rigg ........................ A61Q 1/10 |
| | | | 524/401 |
| 2012/0183861 | A1 | 7/2012 | Gupta et al. |
| 2012/0295987 | A1 | 11/2012 | Misner et al. |
| 2013/0022568 | A1 * | 1/2013 | Adamy ................ A61K 8/8129 |
| | | | 424/70.11 |
| 2013/0319931 | A1 | 12/2013 | Liu et al. |
| 2014/0086970 | A1 | 3/2014 | White |
| 2014/0212598 | A1 | 7/2014 | Curry |
| 2014/0308867 | A1 | 10/2014 | Van Emmerick et al. |
| 2014/0348946 | A1 | 11/2014 | Maki et al. |
| 2015/0064280 | A1 | 3/2015 | Deumal Rubio et al. |
| 2015/0233049 | A1 | 8/2015 | Delattre et al. |
| 2016/0208430 | A1 | 7/2016 | Duffy et al. |
| 2016/0326337 | A1 * | 11/2016 | Farrugia ............ G03G 9/09371 |
| 2017/0006876 | A1 | 1/2017 | Swamy et al. |
| 2017/0065013 | A1 | 3/2017 | Choudhry |
| 2017/0079275 | A1 | 3/2017 | Maki et al. |
| 2017/0314185 | A1 | 11/2017 | Wijesena et al. |
| 2017/0342609 | A1 | 11/2017 | Mandawewala |
| 2018/0020670 | A1 | 1/2018 | Kanovsky |
| 2018/0171542 | A1 | 6/2018 | Lan et al. |
| 2018/0305860 | A1 | 10/2018 | Mondal et al. |

FOREIGN PATENT DOCUMENTS

| | | | |
|---|---|---|---|
| JP | 2004-513246 | A | 4/2004 |
| RU | 2149025 | C1 | 5/2000 |
| RU | 2170080 | C2 | 7/2001 |
| WO | 92/02583 | A1 | 2/1992 |
| WO | 01/94687 | A2 | 12/2001 |

OTHER PUBLICATIONS

Sathyanarayana, M.N. et al., Role of promoters in improving adhesion of organic coatings to a substrate. Progress in Organic Coatings. 26 (1995): pp. 275-313.

Sójka-Ledakowicz et al., Functionalization of textile materials by alkoxysilane-grafted titanium dioxide. Journal of Materials Science. Jul. 2009, vol. 44, Issue 14, pp. 3852-3860.

Webmineral, "Talc mineral Data", Sep. 18, 2016; retrieved on Dec. 28, 2018 from https://web.archive.org/web/20160918211035/http://webmineral.com/data/Talc.shtml; entire document.

International Search Report and Written Opinion of corresponding application PCT/US18/60931, mailed Jan. 24, 2019, all enclosed pages cited.

Supplementary European Search Report, European Application No. 18878246, dated Jul. 27, 2021, 2 pages.

Office Action for Brazilian Application No. 11 2020 009674 1; issued May 3, 2023; (4 Pages).

Preliminary Rejection in Korean App. No. 10-2020-7016648; Issued Apr. 8, 2023 (16 pages).

* cited by examiner

ODOR CONTROL COMPOSITION AND METHOD OF USING

CROSS-REFERENCE TO RELATED APPLICATIONS

This application claims priority from U.S. Provisional Patent Application No. 62/585,749, filed on Nov. 14, 2017, in the United States Patent and Trademark Office. The disclosure of which is incorporated herein by reference in its entirety.

FIELD OF THE INVENTION

The present invention relates to a chemical composition for controlling odor and to a method of using the chemical composition to impart an odor control treatment to an article.

BACKGROUND OF THE INVENTION

Textile binders are chemicals used in fabric pretreatment and textile processing. Textile binders commonly available in the market place are based on acrylates, isocyanate or urethane, silanes, and formaldehyde. However, all the textile binders currently available for use with metal oxides, for example, suffer from at least one of the following disadvantages: high cost, low performance, high curing temperature leading to dyed textile material color fastness degradation, negative impact on other textile properties such as color fastness, softness, moisture wicking performance, and limited to only few fiber types.

Thus, there is need to develop an odor control treatment for textiles that is cost effective, high performing, and can be used to treat a wide range of textile fibers such as polyester, cotton, and nylon.

SUMMARY OF THE INVENTION

The present invention relates to an odor control composition and a method of treatment for textiles.

In an embodiment of the invention, an odor control composition comprising a metal compound selected from the group consisting of a metal oxide, a metal hydroxide, and a combination thereof; and a sulfo polyester is provided.

In an embodiment of the invention, an odor control composition comprising a zinc oxide and a sulfo polyester is provided.

In an embodiment of the invention, a method of using an odor control composition comprising a metal compound selected from the group consisting of a metal oxide, a metal hydroxide, and a combination thereof; and a sulfo polyester is provided. The method comprises applying the odor control composition to a textile material.

In an embodiment of the invention, a method of using an odor control composition comprising a zinc oxide and a sulfo polyester is provided. The method comprises applying the odor control composition to a textile material.

An article comprising a textile material having been treated with an odor control composition comprising a metal compound selected from the group consisting of a metal oxide, a metal hydroxide, and a combination thereof; and a sulfo polyester is provided.

An article comprising a material having been treated with an odor control composition comprising a zinc oxide and a sulfo polyester is provided.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, which are not necessarily to scale, wherein.

DESCRIPTION OF THE PREFERRED EMBODIMENTS

Figure 1:
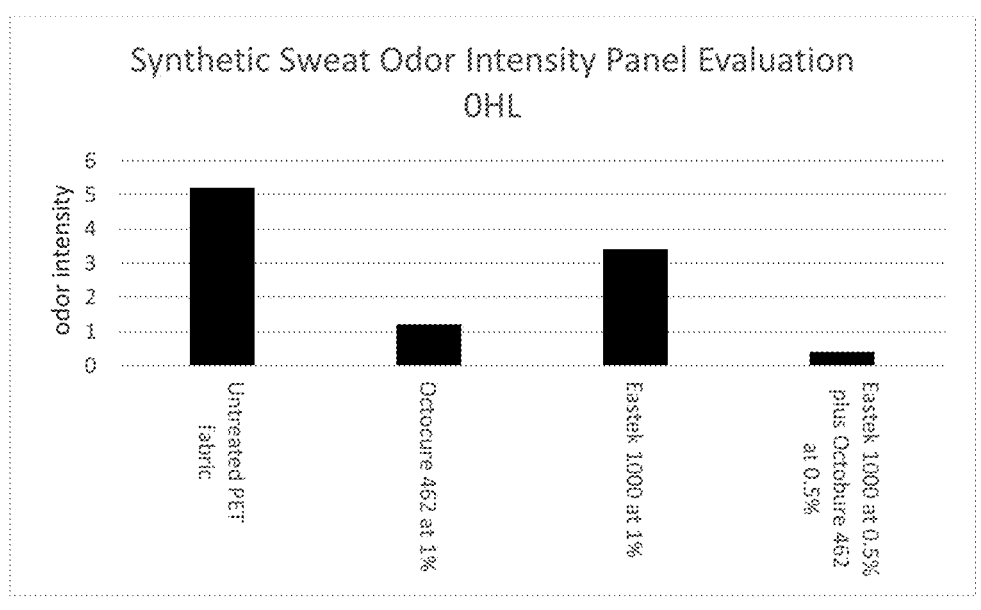
FIG. 1 is a graph illustrating results of a sweat odor panel evaluation in accordance with the present invention.

The following description of the embodiments of the present invention is merely exemplary in nature and is in no way intended to limit the invention, its application, or uses. The following description is provided herein solely by way of example for purposes of providing an enabling disclosure of the invention, but does not limit the scope or substance of the invention.

In an embodiment of the invention, an odor control composition comprises a metal compound selected from the group consisting of a metal oxide, a metal hydroxide, and a combination thereof; and a sulfo polyester.

In the case of a metal oxide, for example, the odor control composition comprises a metal oxide, a sulfo polyester, and a carrier; consists essentially of a metal oxide, a sulfo polyester, and a carrier; and consists of a metal oxide, a sulfo polyester, and a carrier.

Examples of metal oxides suitable for use in the invention include, but are not limited to, zinc oxide, titanium oxide, silver oxide, copper oxide, iron oxide, magnesium oxide, aluminum oxide, and combinations thereof. Metal oxides that are based on transition metals are preferred for the present invention. A preferred metal oxide for use in the present invention is zinc oxide. Alkaline earth metal oxide can also be used in the present invention.

A preferred amount of metal oxide for the present invention is in a range of 0.01 weight % to 3 weight % based on the weight of the textile material, more preferably 0.1 weight % to 2 weight % based on the weight of textile material, and most preferably 0.15 weight % to 1.5 weight % based on the weight of the textile material.

There are other types of metal compounds that could also be used along with the binder in the present invention. Examples of other metal compounds include, but are not limited to, zinc hydroxide, zinc nitrate, silver chloride, magnesium hydroxide, aluminum hydroxide, and combinations thereof.

Sulfo polyester has the properties of a film former, a binder, and a combination thereof. Sulfo polyester is prepared by polymerization of dicarboxylic acids, diols, and a sulfo monomer. Examples of dicarboxylic acids that can be used include isophthalic acid, terephthalic acid, cyclohexanediacetic acid, succinic acid, adipic acid, maleic acid, glutaric acid. Useful diol components of sulfo polyester include but not limited to diethylene glycol, polyethene glycol, butane diol, hexane diol, pentane diol, cyclohexanedimethanol, and the like. The sulfo monomer is a difunctional sulfo monomer. It can be either a dicarboxylic acid or diol containing one or more sulfonate groups. Examples of sulfo monomers include sulfo terephthalic acid, sulfoisophthalic acid. An example of water dispersable sulfo polyester is Eastek sulfo polyester commercially available from Eastman Chemical Company. Examples of commercially available sulfo polyesters include, but are not limited to, Eastek 1000 (30% active), Eastek 1200 (30% active), and Eastek 1400 (30% active).

In an embodiment of the invention, a method of making an odor control composition is provided. In accordance with the method of making the odor control composition, the method comprises combining a metal compound in an aqueous dispersion wherein the metal compound is selected from the group consisting of a metal oxide, a metal hydroxide, and a combination thereof; a sulfo polyester; and a carrier.

A metal oxide aqueous dispersion can be prepared by dispersing a powder metal oxide with a dispersant in a carrier such as water to form a metal oxide liquid dispersion.

Any type of dispersant that is effective to disperse water insoluble particulate inorganic material in a liquid carrier may be used. Examples of dispersants include, but are not limited to, ethoxylated alcohols, polyacrylates, naphthalene formaldehyde condensates, silicone, saline, or clay based dispersants, and combinations thereof.

The liquid carrier is preferably a polar solvent. Examples of polar solvents include, but are not limited to, short to long carbon alcohols, polyethylene glycol, polypropylene alcohol, water, and combinations thereof. More preferably, the polar solvent is water.

In an embodiment of the invention, the odor control composition comprises 0.1 weight percent to 70 weight percent of a metal oxide, 0.1 weight percent to 10 weight percent of a dispersant, and the balance of the weight percentage is a carrier and/or other types of chemicals, wherein the weight percentage is based on the weight percentage of the composition.

In an embodiment of the invention, the odor control composition comprises a zinc oxide aqueous dispersion. Preferably, the odor control composition comprises 0.1 weight percent to 70 weight percent of a zinc oxide, 0.1 weight percent to 10 weight percent of a dispersant, and the balance of the weight percentage is water and/or other types of chemicals, wherein the weight percentage is based on the weight percentage of the composition.

It has been unexpectedly found that sulfo polyester, the binder of the present invention, can also be used as a dispersant by itself or in combination with another dispersant or surfactant.

In an embodiment of the invention, the odor control composition comprises 0.1 weight percent to 70 weight percent of a metal oxide, 0.1 weight percent to 10 weight percent of a sulfo polyester, and the balance of the weight percentage is a carrier and/or other types of chemicals, wherein the weight percentage is based on the weight percentage of the composition.

In an embodiment of the invention, the odor control composition comprises a zinc oxide aqueous dispersion. Preferably, the odor control composition comprises 0.1 weight percent to 70 weight percent of a zinc oxide, 0.1 weight percent to 10 weight percent of a sulfo polyester, and the balance of the weight percentage is water and/or other types of chemicals, wherein the weight percentage is based on the weight percentage of the composition.

The ratio of zinc oxide to sulfo polyester in a formulation combining zinc oxide with sulfo polyester is preferably between 1:10 and 10:1, more preferably between 1:6 and 6:1, and most preferably between 1:3 and 3:1.

Other than metal oxide and sulfo polyester, other functional finishing agents can be added to the composition of the present invention. Example include, but are not limited to, softeners, moisture wicking agents, thickeners, water repellents, antimicrobials, colorants, and fragrances.

In accordance with the present invention, a method of using the odor control composition is provided. The liquid composition comprising metal oxide can optionally be diluted with water and applied onto a textile material using any traditional textile finishing techniques. Examples of traditional textile finishing techniques include, but are not limited to, padding, exhausting, spraying, and roller coating, among others. Non-limiting examples of commercially available zinc oxide metal dispersions are OTOCURE 462, OCTOCURE 573, and OCTOCURE 803 from Tiarco Chemical.

The metal oxide aqueous dispersion is further diluted with water to a desired concentration in order to achieve a targeted loading level of metal oxide aqueous dispersion. For example, a target loading level of metal oxide aqueous dispersion on a textile material is 2 weight % based on dry weight of textile material and the conversion rate or pick up of the diluted aqueous dispersion onto a textile material is 90% with a typical finishing process, the concentration of the metal oxide aqueous composition in the diluted application bath should be 2% divided by 90% equal to 2.22%. As mentioned previously, any wet processing technique can be used to apply the metal oxide aqueous dispersion to a textile material. However, padding is the most preferred application method.

Another component present in the pad bath in accordance with the invention is sulfo polyester. In accordance with the invention, it can be used in the treatment of textile fabrics through padding in a typical textile wet finishing setup. Sulfo polyester is normally supplied as an aqueous dispersion and, therefore, it can be directly added to mixing tank where the pad bath is mixed. The sulfo polyester aqueous dispersion can be added into mixing tank where water has already been added with mixing. The sulfo polyester aqueous dispersion is added either before the addition or following the addition of metal oxide aqueous dispersion in the mixing procedure.

Once the pad bath is mixed in a mixing tank and becomes homogenous, it is pumped into a padding trough and is ready for being padded through the nip of two pressurized rolls onto the textile fabric. Following the padding, a fabric is continuously fed into a drying stenter range to be cured at elevated temperature. The pickup of the metal oxide aqueous dispersion on the fabric can be adjusted by altering the pressure applied on the rolls. The appropriate drying or curing temperature for the application should be between 70 C to 200 C, preferably between 80 C and 170 C and most preferably between 90 C and 150 C.

Sulfo polyester is used as the binder to fix the metal oxides on the textile material once the treatment is dried or cured onto the textile material. The use level of sulfo polyester based on solid is between 0.05 weight % to 4 weight %, preferably from 0.1% to 2%, based on weight of textile material. The weight ratio between metal oxide and sulfopolyester on dry textile materials after treatment should be in the range between 1:15 and 20:1. Preferably, the ratio is between 1:10 and 15:1, and most preferably, the ratio is in the range between 1:3 and 5:1. It has been found that sulfo polyester does not require high curing temperature to adhere appropriately to textile materials. The advantage of being able to cure at low temperature is important for those textile materials where low curing temperature must be used to avoid thermo-migration of dyes, which has been recognized as a major contributor to reduced color fastness for dyed textiles.

In accordance with the invention, a preferred curing temperature for sulfo polyester once being applied onto textile materials is in a range of 70 C to 200 C, more preferably between 80 C and 170 C, and most preferably between 90 C and 150 C.

In an embodiment of the invention, an article having been treated with an odor control composition is provided. The article has a surface having been treated with an odor control composition in accordance with the present invention. The article may be a textile material such as fabric, a building and/or construction material, wood material, and coating material.

Immediate and/or future applications (i.e. end uses) of the invention include, but are not limited to, protection of textiles, and protection of building and construction materials against odors and UV degradation.

Among the reasons that the invention is better and more advantageous than present technology is because of low curing temperature, high performance (more durable to wash than previous binder solutions), applicable to wide variety of textile fibers, and cost effective.

EXAMPLES

Example 1

Figure 2:
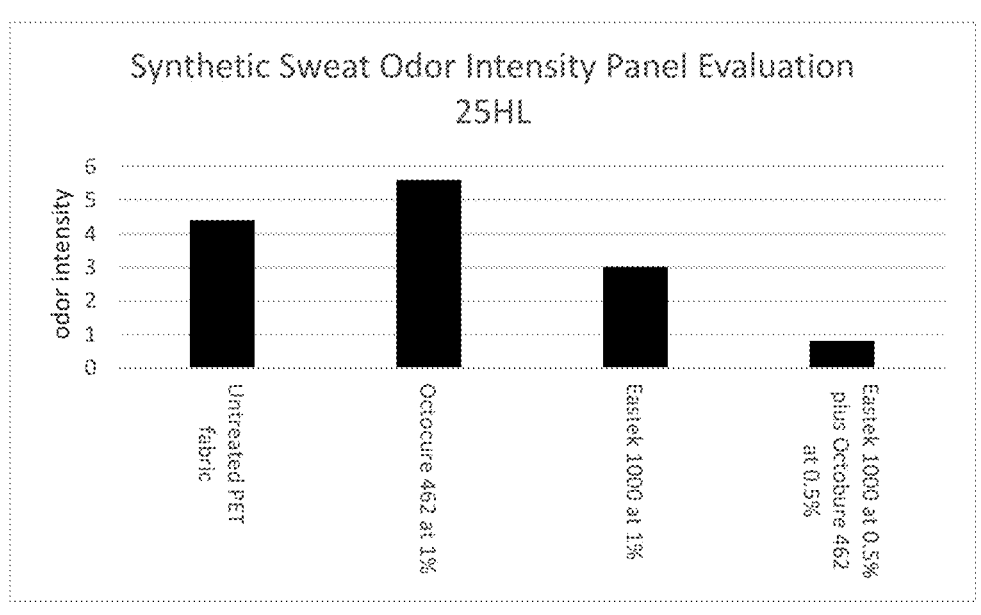
FIG. 2 is a graph illustrating results of a sweat odor panel evaluation in accordance with the present invention.

In this example, a 100% polyester knit fabric obtained from TESTFABRICS was treated through padding with Octocure 462 (0462), a product sold by Tiarco Chemical and/or Eastek 1000 (E1000), a sulfo polyester supplied by Eastman Chemical. The add on level in FIG. 1 and FIG. 2 is expressed as weight percentage of each formulation based on weight of fabric. The padded fabrics were cured with Mathis IR drier at 130 C for 45 seconds. The cured fabrics were then laundered with a home laundering machine using Tide laundry detergent for 25 times. The treated along with untreated control fabric were then assessed for their odor control performance using synthetic sweat developed at Microban Products Company.

The odor strength of fabric exposed to the synthetic sweat was rated based on a scale from 0 to 10 with 0 being no odor and 10 representing extremely strong odor and the results are shown in FIGS. 1 and 2.

In FIG. 1, the fabric treated with combination of Octocure 462 and Eastek 1000 released the least sweat odor among the four treatments (Untreated control fabric, Octocure 463 alone, Eastek 1000 alone, or the combination of Octocure 462 and Eastek 1000). These fabrics were not laundered but inoculated with synthetic sweat. FIG. 2 displays sweat odor rating of fabrics washed in a home laundering machine for 25 times and then inoculated with synthetic sweat. This time only the fabric treated with combination of Octocure 462 and Eastek 1000 suppressed sweat odor generation in fabric after 25 home launderings and the rest of the treatments failed to control odor development on fabric. The data clearly demonstrated that there is a synergy between Octocure 462 or zinc oxide and Eastek 1000 or sulfo polyester in inhibiting sweat odor generation in textiles and the synergy effect is also durable to home launderings.

X-ray fluorescence (XRF) analysis was also used to determine the active zinc levels on fabric treated with Octocure 462 and/or Eastek 1000 after 25 home launderings, and the results are listed in Table 1. XRF spectrometry is an elemental metal analysis technique used in identification and quantitative analysis of metals in coatings. XRF is based on the principle that individual atoms, when excited by an external energy source, emit X-ray photons of a characteristic energy or wavelength. By counting the number of photons of each energy emitted from a sample, the elements present may be identified and quantitated. The XRF analysis results show that the active zinc level of fabric treated with combination of Octocure 462 and Eastek is much higher than the other treatments after the fabrics were washed 25 times.

TABLE 1

| Fabric Treatment Types | XRF of zinc on polyester fabric after 25 home launderings (ppm) |
|---|---|
| Untreated PET fabric | 18 |
| Octocure 462 at 1% | 40 |
| Eastek 1000 at 1% | 30 |
| Octocure 462 at 0.5% plus Eastek 1000 at 0.5% | 1000 |

Example 2

In this example, an aqueous zinc oxide formulation was made using sulfo polyester as a dispersant. The composition of the formulation is listed in Table 2.

TABLE 2

| Weight % of each component in the aqueous formulation | Premade concentrated formulation |
|---|---|
| Eastek 1000 | 59.95 |
| Xiameter OFX 5211 (a silicone based surfactant) | 0.05 |
| zinc oxide powder | 40 |

The premade formulation was then diluted with water to a pad bath comprising 97% water and 3% premade formulation. The pad bath was then padded onto polyester, cotton, and nylon fabrics with a laboratory padding machine. After the padding, fabrics were cured at 130 C using an IR drier. Fabrics were then washed and the active zinc level on the fabric was determined with XRF analysis. The results are listed in Table 3.

TABLE 3

| XRF Zinc 25HL (ppm) | Polyester | Nylon | Cotton |
|---|---|---|---|
| Zinc oxide formulation at 3% based on fabric weight | 4579 | 2080 | 968 |
| Fabric without treatment | Not detectable | Not detectable | Not detectable |

Figure 3:
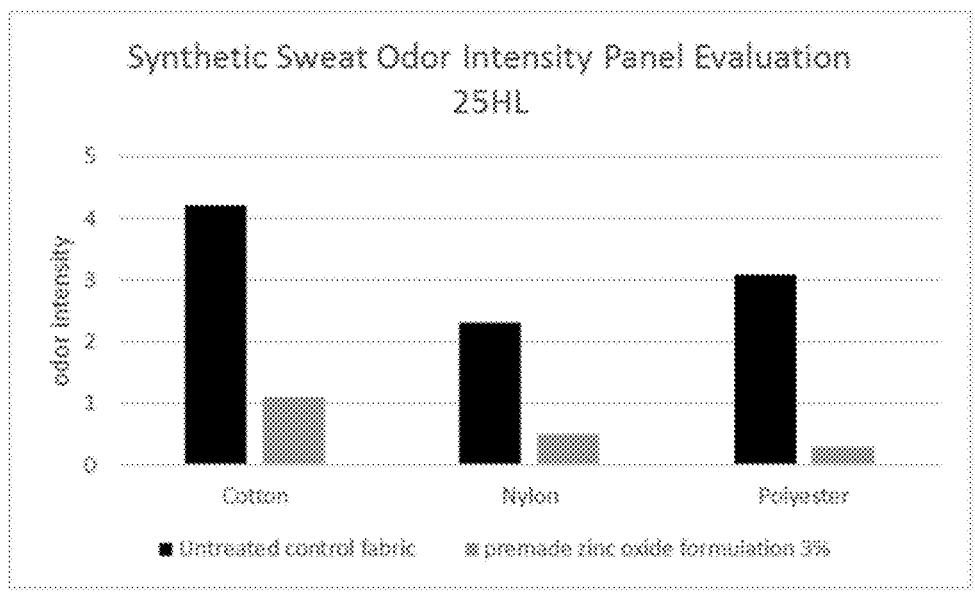
FIG. 3 is a graph illustrating odor control performance of treated fabric compared with untreated fabric using data obtained from a synthetic sweat odor panel evaluation.

XRF results in Table 3 show that the zinc levels on fabric after 25 HL are at least 900 ppm dependent on fabric types. Based on our experience, the zinc level of 900 ppm is more than high enough for achieving a good odor control performance in textiles. The odor control performance of treated fabrics is confirmed in FIG. 3 where the odor control performance of treated fabric is compared with untreated fabric using the data obtained from the synthetic sweat panel evaluation. The synergistic odor control performance with combination of Octocure 462 and Eastek 1000 can therefore be demonstrated not only on polyester textile fibers but also on other types of fibers.

Example 3

In this example, sulfo polyester was compared with polyacrylic binders on improving the wash durability of zinc oxide treatment on polyester fabric. Polyacrylic binder Rhoplex TR-934 HS and Rhoplex TR-407 were obtained from Dow Chemical Company. The polyester fabric was treated with formulations in Table 4 through padding and cured at 130 C for 45 seconds afterward. The treated fabrics were then laundered 25 times and then the zinc levels on fabric were measured with XRF for durability.

TABLE 4

| Weight % of each component in pad bath | Formula 1 | Formula 2 | Formula 3 | Formula 4 |
|---|---|---|---|---|
| Water | 99% | 98.9% | 99.17% | 97.00% |
| Octocure 462 | 0.5% | 0.5% | 0.5% | 1.5% |
| Eastek 1000 | 0.5% | 0% | 0% | 1% |
| Rhoplex TR-934 HS | 0% | 0.6% | 0% | 0% |
| Rhoplex TR-407 | 0% | 0% | 0.33% | 0% |
| Evosoft HSP | | | | 0.5% |
| 50% Citric acid in water | | | | Enough to adjust pH of pad bath to 6.54 |

It should be noted that the weight percentage of each binder on fabric was kept the same as 0.15% for each treatment for a fair comparison.

The pH of treatment bath of Formula 4 was adjusted with citric acid from alkaline pH to a neutral or slightly acidic pH. Any type of acids can be used to adjust the pH of zinc oxide treatment bath. The useful acids include but are not limited to inorganic acids or organic acids where organic acids may be preferred. Examples of useful acids include but not limited to sulfuric acid, nitric acid, acetic acid, tannic acid, formic acid, succinic acid, ethylenediaminetetraacetic acid, and polyacrylic acid.

TABLE 5

| | XRF zinc ppm analysis of polyester fabric after 25 home launderings |
|---|---|
| Formula 1 | 1015 |
| Formula 2 | 342 |
| Formula 3 | 193 |
| Formula 4 | 1835 |

The XRF tests results in Table 5 demonstrates that sulfo polyester is much superior to acrylic binders in locking durable zinc oxide in the fabric and make it durable to home launderings.

Example 4

In this example, sulfo polyester was compared with polyacrylic acid at binding zinc oxide to nylon fabric and making it resistant to home launderings. The polyacrylic acid used in this example is a Microban binder R10950. Nylon fabric, texturized Nylon 6.6 stretch, was obtained from Testfabrics, Inc. The pad bath formulations listed in Table 6 were prepared first and then padded onto the fabric followed with curing at 130° C. for 45 seconds. Treated fabrics were laundered 25 times and assessed for their wash durability subsequently with XRF analysis. Results are displayed in Table 7

TABLE 6

| | Formula 5 | Formula 6 |
|---|---|---|
| Water | 99% | 99% |
| Octocure 462 | 0.5% | 0.5% |
| Eastek 1000 | 0.5% | 0% |
| R10950 | 0 | 0.5% |

TABLE 7

| | XRF on nylon fabric after 25 home launderings (ppm) |
|---|---|
| Formula 5 | 360 |
| Formula 6 | 108 |

Once again, sulfo polyester was shown to be a much better binder for use to fix zinc oxide permanently on nylon fabric than polyacrylic binder.

Example 5

In this example, Octocure 462 and Eastek 1000 were exhausted onto a black dyed polyester rich fabric comprising 81% polyester and 19% spandex. The exhaustion was performed in a beaker dyeing machine, Lobomat BFA-24, Werner Mathis AG. The exhaustion conditions are listed in Table 8. BC300A was 1% based on weight of fabric and BC300B was also 1% based on weight of fabric.

TABLE 8

| Parameters | Set conditions |
|---|---|
| Liquor ratio (water to fabric on weight) | 10 to 1 |
| Exhaustion temperature | 90° C. |
| Dwell time at the exhaustion temperature | 20 min |
| Heating rate | 2 C./min |
| Cooling rate | 6 C./min |
| pH of exhaustion bath | 6.73 adjusted with citric acid |
| Curing temperature | 130° C. |

Figure 4:
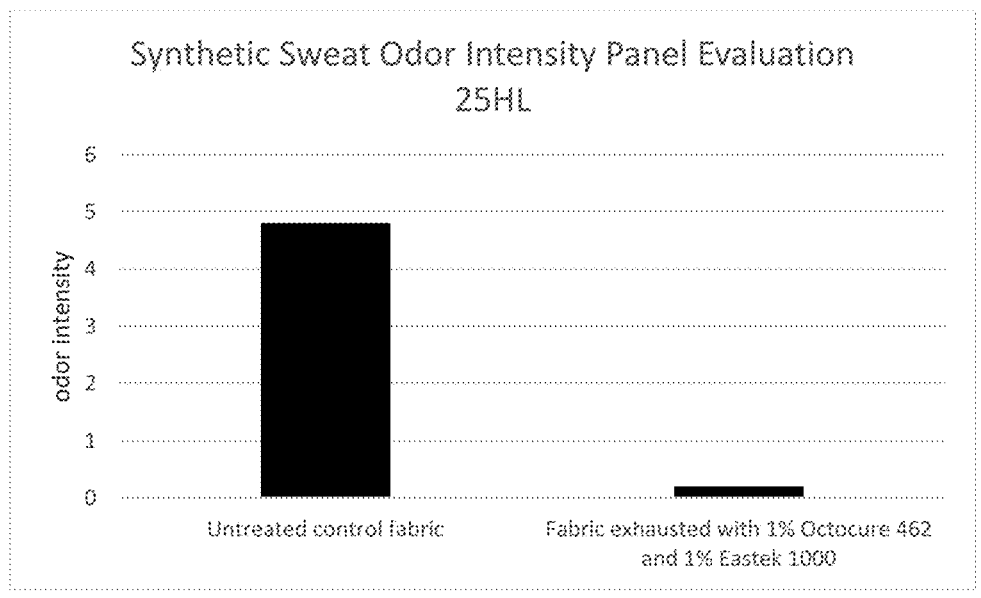
FIG. 4 is a graph illustrating results of a sweat odor panel evaluation in accordance with the present invention.

After exhaustion, the fabric was extracted and cured. The odor control performance and durability of the treatment were evaluated with sweat odor panel in FIG. 4. It was shown that the fabric treated with Octocure 462 and Eastek 1000 through exhaustion provides significant odor control performance and it is resistant to washing.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What is claimed is:

1. An odor control composition for application and treatment of a textile material that maintains color-fastness of the textile material during and post application thereto, the odor control composition comprising:
   zinc oxide,
   a sulfo polyester, and
   a pH adjuster,
      wherein:
   the odor control composition is an aqueous dispersion,
   the odor control composition comprises from 97 wt % to 99 wt % water, and
   the zinc oxide to sulfo polyester is present in a weight ratio of 10:1 to 2:1.

2. The odor control composition according to claim 1, wherein zinc oxide is present in a range of 0.01 weight % to 3 weight % based on weight of a textile material.

3. The odor control composition according to claim 2, wherein zinc oxide is present in a range of 0.1 weight % to 2 weight % based on weight of the textile material.

4. The odor control composition according to claim 3, wherein zinc oxide is present in a range of 0.15 weight % to 1.5 weight % based on weight of the textile material.

5. The odor control composition according to claim 1, wherein the sulfo polyester is prepared by polymerization of a dicarboxylic acid, diol, and a sulfo monomer.

6. The odor control composition according to claim 5, wherein the dicarboxylic acid is selected from the group consisting of isophthalic acid, terephthalic acid, cyclohexanediacetic acid, succinic acid, adipic acid, maleic acid, glutaric acid, and a combination thereof.

7. The odor control composition according to claim 5, wherein the diol is selected from the group consisting of diethylene glycol, polyethene glycol, butane diol, hexane diol, pentane diol, cyclohexanedimethanol, and a combination thereof.

8. The odor control composition according to claim 5, wherein the sulfo monomer is a difunctional sulfo monomer.

* * * * *